United States Patent [19]

Bostick

[11] Patent Number: 5,334,326
[45] Date of Patent: Aug. 2, 1994

[54] DIAROYL PEROXIDE COMPOSITIONS

[75] Inventor: John V. Bostick, San Dimas, Calif.

[73] Assignee: Norac Company, Inc., Azusa, Calif.

[21] Appl. No.: 737,069

[22] Filed: Jul. 29, 1991

[51] Int. Cl.$^5$ .................................. C01B 15/055
[52] U.S. Cl. .......................... 252/186.26; 252/186.25; 252/186.42
[58] Field of Search ............ 252/186.26, 186.42, 252/186.25

[56] References Cited

U.S. PATENT DOCUMENTS

| | | | |
|---|---|---|---|
| Re. 28,818 | 5/1976 | Eymans et al. | 252/186 |
| 2,454,254 | 2/1944 | Kuoch | 252/186.29 |
| 3,181,991 | 5/1965 | Leveskis | 252/430 |
| 3,182,026 | 5/1965 | Leveskis | 252/430 |
| 3,507,800 | 4/1970 | Leveskis | 252/186 |
| 3,538,011 | 11/1970 | van der Klaauw | 252/186 |
| 3,723,336 | 3/1973 | Eymans et al. | 252/186 |
| 3,795,630 | 5/1974 | Jaspers et al. | 252/426 |
| 4,255,277 | 3/1981 | Smearing | 252/186.29 |
| 4,465,755 | 8/1984 | Kiritani et al. | 430/111 |

OTHER PUBLICATIONS

Aztec Chemicals, Technical Data Bulletin PB-3B.
Witco Chemical, Technical Bulletin BLQ-50, BZQ55.
Noury Chemicals, Chemicals for Plastic and Elastomers, Bulletin 85-12.
Lucidol, Product Bulletin 1.104, Product Bulletin 1.105.
Lucidol, Product Bulletin 1.107.

Primary Examiner—Richard D. Lovering
Assistant Examiner—Joseph D. Anthony

[57] ABSTRACT

The use of alkyl benzoates in which the alkyl group has 8 to 12 carbon atoms, to prepare diaroyl peroxide compositions with improved stability and good processing characteristics is disclosed.

7 Claims, No Drawings

DIAROYL PEROXIDE COMPOSITIONS

This invention relates to new compositions of diaroyl peroxides with improved chemical stability utilizing medium chain length alkyl benzoates.

This invention further relates to the preparation of liquid and paste compositions of diaroyl peroxides particularly dibenzoyl peroxide, utilizing alkyl benzoates as a vehicle in which the alkyl group has between 8 to 12 carbon atoms.

Diaroyl peroxides and especially dibenzoyl peroxide are employed For many uses such as polymerization initiators in the preparation of vinyl polymers, curing agents for unsaturated resins and as bleaching agents. Most diaroyl peroxides and particularly dibenzoyl peroxide are hazardous in the dry crystalline form and therefore require a phlegmatizer or desensitizer to facilitate their safe handling. While solid diluents are used in a few applications diaroyl peroxides are commonly formulated as a paste or as a liquid suspension in order to facilitate their use and make them commercially acceptable.

A range of vehicles which also function as phlegmatizers, have been employed in the preparation of the compositions. One of the earliest was tricresyl phosphate which still is very useful for a few applications but has been replaced in most uses. Vehicles which are most commonly used are esters of ortho-phthalic acid such as butyl benzyl phthalate, dibutyl phthalate and diisobutyl phthalate. Benzoates of glycols particularly dipropylene glycol dibenzoate have also been employed.

The diaroyl peroxides such as benzoyl peroxide when manufactured, are small granules which are agglomerates of many very fine crystals. An important property in the selection of a vehicle for an aroyl peroxide composition is that it softens the granules so that they disperse or break down readily into the individual crystals in the vehicle when mixed. This eliminates the necessity of milling the composition in order to reduce particle size to make them economically acceptable. Thus one of the requirements of a suitable vehicle is that it softens or disperses the granules readily. Another requirement is that the aroyl peroxide be sufficiently stable when in contact with the vehicle over the temperature range normally encountered in commercial applications, shipping and use to prevent gassing, loss of activity during storage and shipping and minimization of any potential for an exothermic self accelerating decomposition.

Diaroyl peroxides of which dibenzoyl peroxide is a primary example, in their dry crystalline state or in contact with water are much more thermally stable than when in contact with an organic vehicle. With some organic vehicles such as propylene glycol for example they have good stability, but propylene glycol has the disadvantage that it does not soften the granules so that they disperse readily through mixing into the individual crystals Therefore, the diaroyl peroxide must be milled prior to use or the composition must milled after preparation, which are expensive and tedious operations. In addition, propylene glycol is not acceptable in some applications.

In addition to the organic vehicle, water is an ingredient in many diaroyl peroxide formulations. The water reduces the hazard from burning and is an energy absorber or sink when decomposition occurs.

The term "stability" as used herein unless otherwise indicated refers to "chemical stability" at those temperatures and conditions potentially encountered in storage, transport and use. In the organic peroxide literature the term stability has also been used to describe the potential for explosive decomposition, and in compositions such as pastes, liquid suspensions and emulsions, it has been used to refer to the potential or rate of separation of the vehicles or the breaking of an emulsion. Chemical stability relates to the loss of activity (decomposition) with time. Since heat is evolved during the decomposition of diaroyl peroxides, the rate of decomposition (which increases with temperature) also determines the temperature at which a composition can be shipped, stored or used.

Improved chemical stability is of great importance since the Department of Transportation and the United Nations have established the rule that all organic peroxide compositions that are to be shipped without temperature control must pass a 50° C. stability test without undergoing a self accelerating decomposition (SADT). Many current diaroyl peroxide compositions including dibenzoyl peroxide compositions are marginal or fail in larger packages.

It is also important commercially that the loss of assay or product by decomposition be at a minimum during storage and transport since the concentration of diaroyl peroxide used determines the rate of polymerization, the properties and quality of the product produced.

This invention involves the discovery that medium chain alkyl esters of benzoic acid in which the alkyl group has from 8 to 12 carbon atoms gives compositions with diaroyl peroxides that have improved chemical stability and good processibility. While alkyl benzoates in which the alkyl group contained 8 to 12 carbon atoms were found to be effective benzoate esters with alkyl groups containing 9 to 11 carbon atoms are more effective and 10 carbon atoms is optimum. The preferred ester is isodecyl benzoate in improving chemical stability and having excellent workability. The improvement in chemical stability falls off as the alkyl chain shortens and the workability as the alkyl groups lengthens.

Diaroyl peroxides in general are stabilized. Examples of which are ortho- and para-methyl and 2,4-dichloro derivatives of dibenzoyl peroxide. However by far the most important and fortunately highly stabilized is (unsubstituted) dibenzoyl peroxide.

While the compositions appear to show stabilization at all ratios, the practical effective ratio of diaroyl peroxide to alkyl benzoate is from 7-1 to 1 0.3-1 with 6-1 to 1.25-1 being a more common range The improved chemical stability observed with compositions of diaroyl peroxides and C-8 to C-12 alkyl benzoates was found to be very general and functional within the wide range of compositions used in the art. Thus the presence or absence of water, pigments, thixotropic agents, emulsifiers and inorganic fillers does not change substantially the observed improvement in stability compared to similar compositions with other vehicles.

The invention will be further described by reference to the following examples which set forth the specific embodiments of the present invention. These embodiments however, are merely illustrative and not to be construed as limitative of the present invention.

EXAMPLE 1

Liquid dispersions were prepared from benzoyl peroxide 40 g, water 16 g, hydrophobic pyrogenic silica 2 g, and an organic vehicle 42 g. Fifty grams of each dispersion in tightly sealed, polypropylene jars were placed in a circulating air oven at 50° C. The assay was determined periodically as given.

| Vehicle | Initial assay Benzoyl peroxide | Percent loss after 4 days | 8 days |
|---|---|---|---|
| Butyl benzyl phthalate | 40.4% | 15.6 | 18.3 |
| Dibutyl phthalate | 39.3 | 6.7 | 14.5 |
| Isodecyl benzoate | 39.5 | 5.6 | 11.6 |

EXAMPLE 2

Paste formulations were prepared from 50 g of benzoyl peroxide, 18 g of water, 2 g of a hydrophobic pyrogenic silica, 5 g of a polyoxypropylenepolyoxyethylene butyl ether and 25 g of a vehicle. Seventy gram portions in tightly sealed polypropylene jars were placed in an air circulating oven at 50° C. and the loss due to decomposition determined over time.

| Vehicle | Initial assay Benzoyl peroxide | Percent loss after |
|---|---|---|
| I | | 5 days |
| Butyl benzyl phthalate | 49.9% | −6.4 |
| Dibutyl phthalate | 50.6 | −5.5 |
| Isodecyl benzoate | 50.6 | −4.0 |
| n-Octyl benzoate | 50.4 | −5.8 |
| Dipropylene glycol dibenzoate | 51.3 | −5.1 |
| II | | 3 days |
| Diisobutyl phthalate | 51.1 | −6.5 |
| Isodecyl benzoate | 50.6 | −3.8 |

EXAMPLE 3

Paste formulations were prepared from 10 g of benzoyl peroxide and 10 g of vehicle. Twenty gram portions were placed in an air circulation oven at 50° C.

| Vehicle | Initial assay Benzoyl peroxide | Percent loss after 4 days |
|---|---|---|
| Butyl benzyl phthalate | 50.4% | 4.6 |
| Isodecyl benzoate | 50.3 | 3.4 |

EXAMPLE 4

Benzoyl peroxide paste formulations (400 ml) with the same composition as in example 2 were heated to 48°–50° C. and placed in preheated high efficiency Dewar flasks. The flasks were placed in an air circulated oven at 50° C. and

| Vehicle | Time 50° C. to peak exotherm |
|---|---|
| Butyl benzyl phthalate | 32 hr. |
| Dibutyl phthalate | 30 |
| Isodecyl benzoate | 81 |
| n-Octyl benzoate | 67 |

EXAMPLE 5

Colored pastes prepared similarly to Example 2 but with variations in emulsifier and thixotropic agents to adjust for the differences in the properties of the pigments, color and vehicle were heated at 50° C. in an oven according to the procedure for testing set forth in the United Nations*.

| | Color | Vehicle | Result |
|---|---|---|---|
| 1 | Red[a] | Butyl benzyl phthalate | Fail |
| 2 | Blue[b] | " | " |
| 3 | White[c] | " | " |
| 4 | Red[d] | " | " |
| 5 | Red[a] | Isodecyl benzoate | Pass |
| 6 | Blue[b] | " | " |
| 7 | White[c] | " | " |
| 8 | Red[d] | " | " |

[a]iron oxide pigment
[b]Prussian Blue pigment
[c]no pigment
[d]C.I. Pigment Red 144
*Recommendations on the Transportation of Dangerous Goods, Tests and Criteria, Second Edition, Tests and Criteria for the Classification of Organic Peroxides Part II, Section 4.

EXAMPLE 6

Wet benzoyl peroxide (assay 75%) 670 g, was mixed for five minutes in a covered Hobart type mixer with 250 g of one of the vehicles listed below. At the end of five minutes the mixing was stopped to prevent over heating and the condition of the mixture observed at intervals for the next hour.

| Vehicle | Conditions of mixture |
|---|---|
| Butyl benzyl phthalate | smooth paste at 5 minutes |
| Dibutyl phthalate | grainy after 30 minutes |
| | slightly grainy after 1 hour* |
| Isodecyl benzoate | smooth paste at 5 minutes |
| n-Octyl benzoate | smooth paste at 5 minutes |
| Dipropylene glycol dibenzoate | grainy after 30 minutes |
| | smooth paste after 1 hour |
| Diisobutyl phthalate | grainy after 30 minutes |
| | slightly grainy afte 1 hour* |

*These compositions made smooth pastes when mixed vigorously after these time periods.

I claim

1. A stabilized paste or liquid dispersion comprising: (1) a diaroyl peroxide, (2) a liquid alkyl ester of benzoic acid in which the alkyl group of the ester has from 8 to 12 carbon atoms, and (3) water from 0.0 to 40% by weight; said diaroyl peroxide is readily dispersible and essentially insoluble, and the ratio of said diaroyl peroxide to the said alkyl benzoate is from 0.3-1 to 7-1.

2. The composition of claim 1 in which the diaroyl peroxide is benzoyl peroxide.

3. The composition of claim 2 in which the alkyl group has from 9 to 11 carbon atoms.

4. The composition of claim 3 in which the alkyl group has 10 carbon atoms.

5. The composition of claim 4 in which alkyl benzoate is isodecyl benzoate.

6. The composition of claim 5 in which the ratio of benzoyl peroxide to isodecyl benzoate is from 6-1 to 1.25-1.

7. A stabilized paste or liquid dispersion consisting essentially of: (1) a diaroyl peroxide, (2) a liquid alkyl ester of benzoic acid in which the alkyl group of the ester has from 8 to 12 carbon atoms, and (3) water from 0.0 to 40% by weight; said diaroyl peroxide is readily dispersible and essentially insoluble, and the ratio of said diaroyl peroxide to the said alkyl benzoate is from 0.3-1 to 7-1.

* * * * *